US00PP37571P2

(12) United States Plant Patent
Mathey

(10) Patent No.: US PP37,571 P2
(45) Date of Patent: Aug. 11, 2026

(54) ***CALLICARPA* PLANT NAMED 'SMNCJLIEP'**

(50) Latin Name: *Callicarpa japonica*
Varietal Denomination: SMNCJLIEP

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 19/383,641

(22) Filed: Nov. 8, 2025

(51) Int. Cl.
*A01H 5/08* (2018.01)
*A01H 6/50* (2018.01)

(52) U.S. Cl.
USPC ..... Plt./226

(58) Field of Classification Search
USPC ..... Plt./226

CPC ... A01H 5/08; A01H 5/02; A01H 5/00; A01H 6/50

See application file for complete search history.

(56) References Cited

PUBLICATIONS

Spring Meadow Early Amethyst, retrieved on Mar. 10, 2026 at https://springmeadownursery.com/plantfinder/early-amethyst-08150, 2 pp. (Year: 2026).*

* cited by examiner

*Primary Examiner* — June Hwu
(74) *Attorney, Agent, or Firm* — C. Anne Whealy

(57) ABSTRACT

A new and distinct cultivar of *Callicarpa* plant named 'SMNCJLIEP', characterized by its uniform, upright and columnar plant habit; vigorous growth habit; rapid growth rate; freely branching habit; medium green-colored leaves; freely flowering and fruiting habit; numerous glossy reddish purple-colored flowers; and good garden performance.

4 Drawing Sheets

Figure 1:
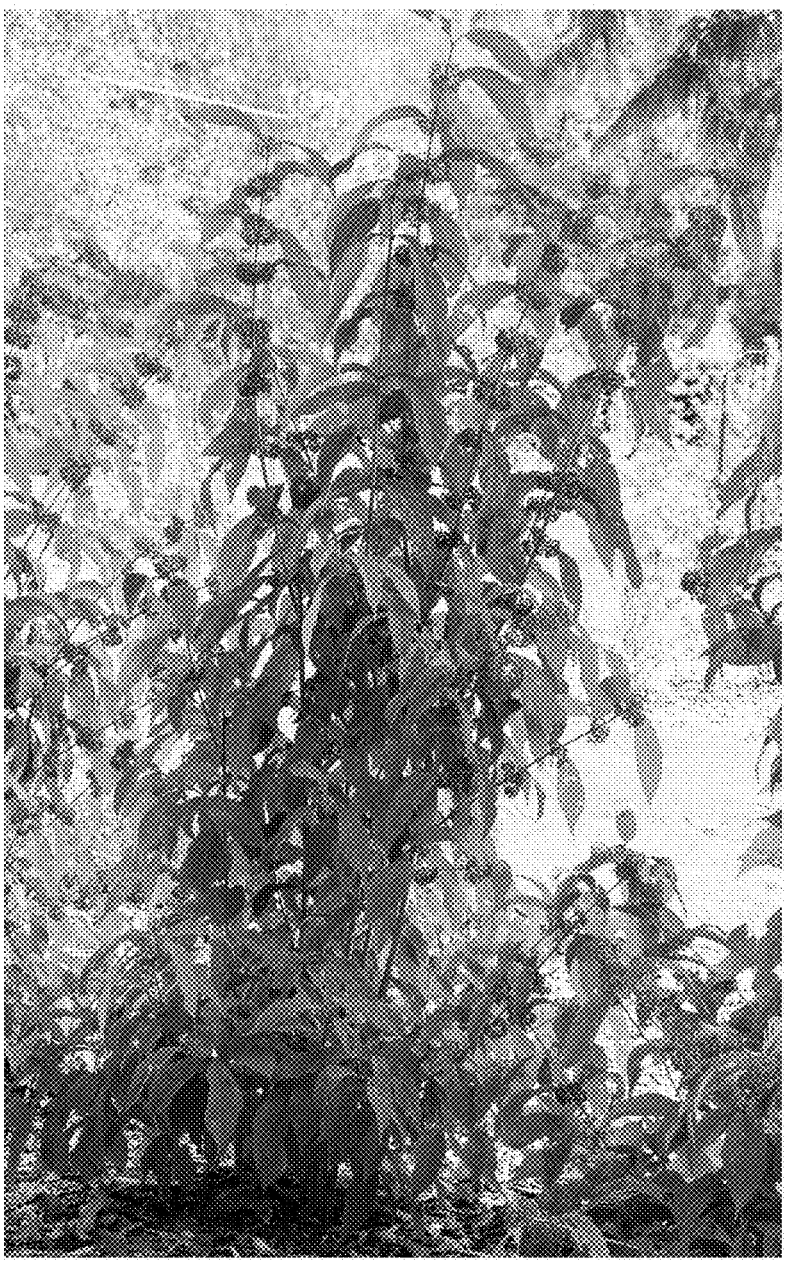

Botanical designation: *Callicarpa japonica.*
Cultivar denomination: 'SMNCJLIEP'.

BACKGROUND OF THE INVENTION

The present invention relates to a new and distinct cultivar of *Callicarpa* plant, botanically known as *Callicarpa japonica*, commonly referred to as Japanese Beautyberry and hereinafter referred to by the name 'SMNCJLIEP'.

The new *Callicarpa* is a product of a planned breeding program conducted by the Inventor in Grand Haven, Michigan. The objective of the breeding program was to develop new uniform and freely branching *Callicarpa* plants with numerous fruits.

The new *Callicarpa* plant originated from an open-pollination during the summer of 2018 of *Callicarpa japonica* 'Heavy Berry', not patented, as the female, or seed, parent with an unknown proprietary selection of *Callicarpa japonica* as the male, or pollen, parent. The new *Callicarpa* plant was discovered and selected by the Inventor during the summer of 2020 as a single flowering plant within the progeny of the stated open-pollination in a controlled environment in Grand Haven, Michigan.

Asexual reproduction of the new *Callicarpa* plant by softwood cuttings in a controlled greenhouse environment in Grand Haven, Michigan since the summer of 2020 has shown that the unique features of this new *Callicarpa* plant are stable and reproduced true to type in successive generations of asexual reproduction.

SUMMARY OF THE INVENTION

Plants of the new *Callicarpa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNCJLIEP'. These characteristics in combination distinguish 'SMNCJLIEP' as a new and distinct *Callicarpa* plant:

1. Uniform, upright and columnar plant habit.
2. Vigorous growth habit and rapid growth rate.
3. Freely branching habit.
4. Medium green-colored leaves.
5. Freely flowering and fruiting habit.
6. Numerous glossy reddish purple-colored flowers.
7. Good garden performance.

Plants of the new *Callicarpa* can be compared to plants of the female parent, 'Heavy Berry'. In side-by-side comparisons, plants of the new *Callicarpa* differ primarily from plants of 'Heavy Berry' in the following characteristics:

1. Plants of the new *Callicarpa* are denser than and not as open and rangy as plants of 'Heavy Berry'.
2. Plants of the new *Callicarpa* are more freely fruiting than plants of 'Heavy Berry'.

Plants of the new *Callicarpa* can also be compared to plants of *Callicarpa dichotoma* 'Early Amethyst', not patented. In side-by-side comparisons, plants of the new *Callicarpa* differ primarily from plants of 'Early Amethyst' in the following characteristics:

1. Plants of the new *Callicarpa* are more upright than and not as rounded as plants of 'Early Amethyst'.
2. Plants of the new *Callicarpa* are denser than and not as open and rangy as plants of 'Early Amethyst'.

3. Plants of the new *Callicarpa* are more freely fruiting than plants of 'Early Amethyst'.

BRIEF DESCRIPTION OF THE PHOTOGRAPHS

The accompanying colored photographs illustrate the overall appearance of the new *Callicarpa* plant showing the colors as true as it is reasonably possible to obtain in colored reproductions of this type. Colors in the photographs may differ slightly from the color values cited in the detailed botanical description which accurately describe the colors of the new *Callicarpa* plant.

The photograph on the first sheet (FIG. 1) is a side perspective view of a typical fruiting plant of 'SMNCJLIEP' grown in an outdoor nursery during the summer.

Figure 2:
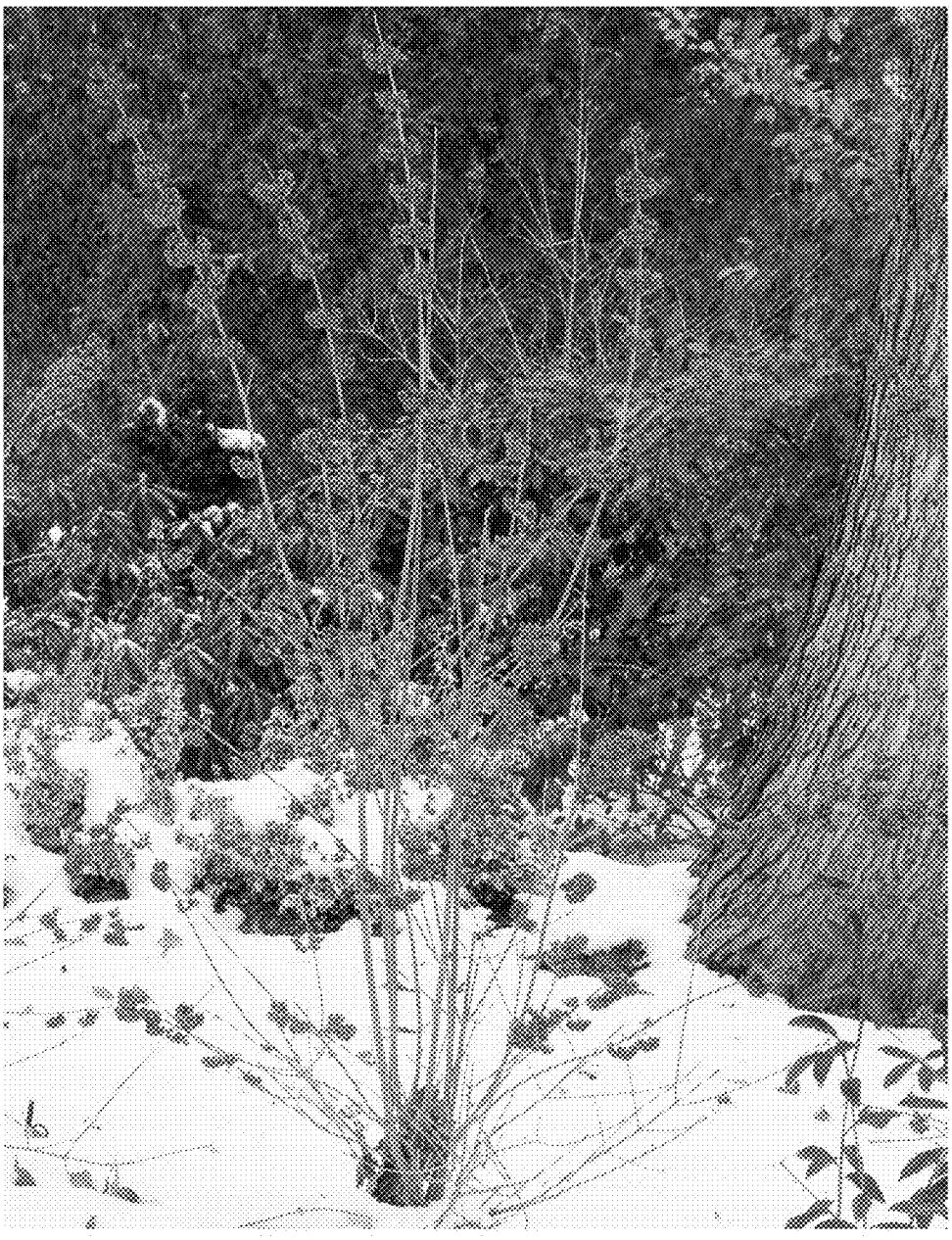

The photograph on the second sheet (FIG. 2) is a side perspective view of a typical fruiting plant of 'SMNCJLIEP' grown in an outdoor nursery during the winter.

Figure 3:
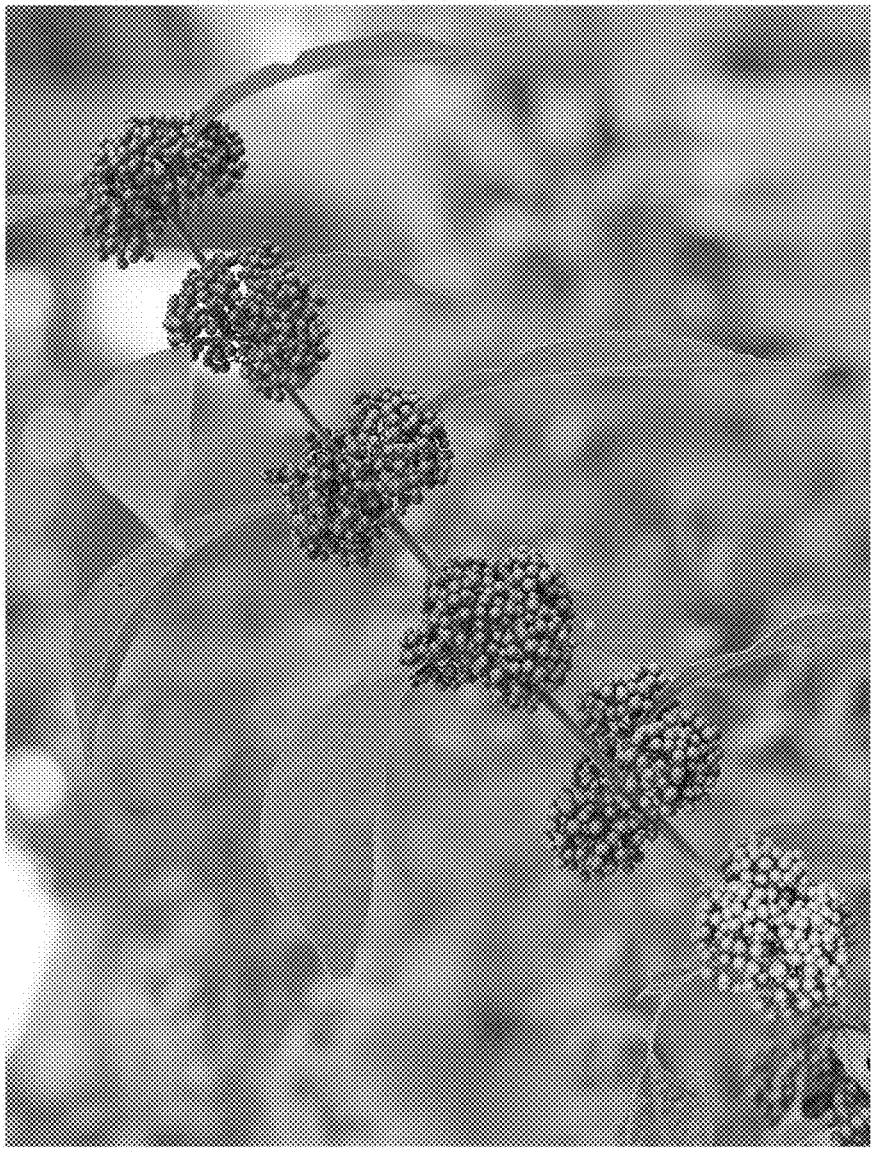

The photograph on the third sheet (FIG. 3) is a close-up view of a typical fruiting stem of a plant of 'SMNCJLIEP' grown in an outdoor nursery.

Figure 4:
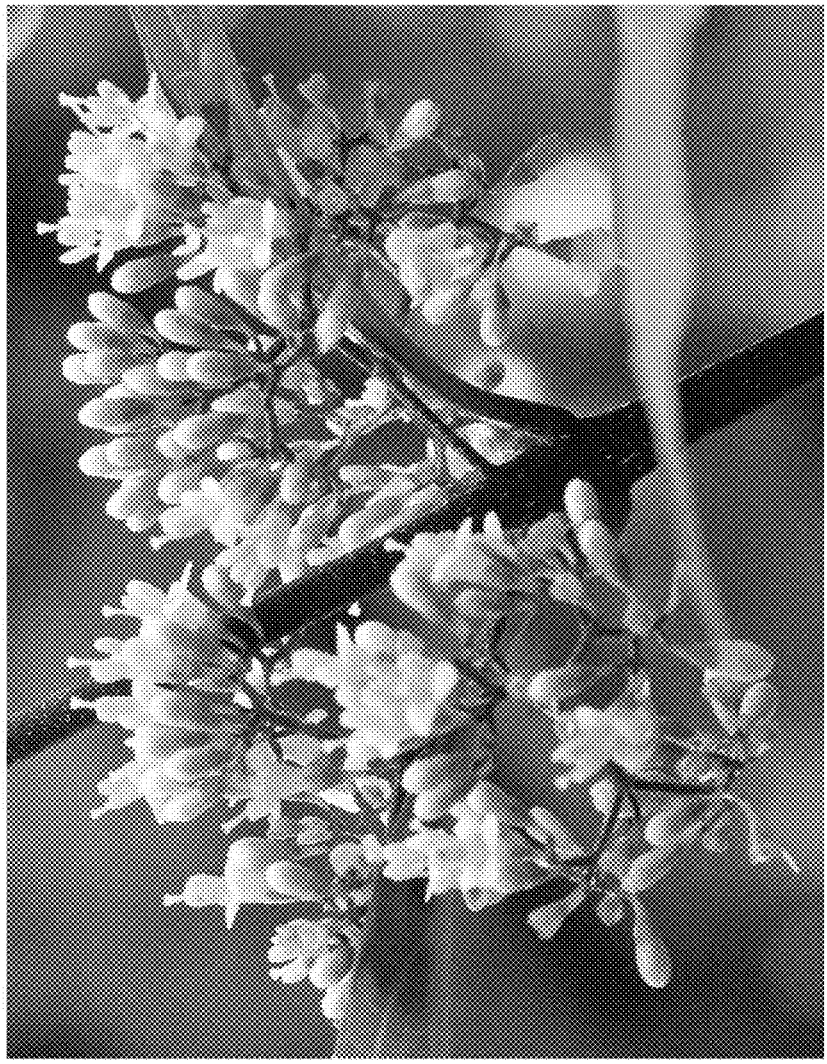

The photograph on the fourth sheet (FIG. 4) is a close-up view of a typical flowering stem of a plant of 'SMNCJLIEP' grown in an outdoor nursery.

DETAILED BOTANICAL DESCRIPTION

The following observations, measurements and values describe plants grown during the summer in three-gallon containers in a polyethylene-covered greenhouse in Grand Haven, Michigan and under cultural practices typical of commercial *Callicarpa* production. During the production of the plants, day temperatures ranged from 18° C. to 27° C. and night temperatures ranged from 5° C. to 10° C. Plants were three years old when the detailed description was taken. In the description, color references are made to The Royal Horticultural Society Colour Chart, 2015 Edition, except where general terms of ordinary dictionary significance are used.

Botanical classification: *Callicarpa japonica* 'SMNCJLIEP'.

Parentage:

*Female, or seed, parent.*—*Callicarpa japonica* 'Heavy Berry', not patented.

*Male, or pollen, parent.*—Unknown proprietary selection of *Callicarpa japonica*, not patented.

Propagation:

*Type.*—By softwood cuttings.

*Time to initiate roots, summer.*—About four weeks at temperatures ranging from 18° C. to 27° C.

*Time to produce a rooted young plant, summer.*—About 40 to 60 days at temperatures ranging from 18° C. to 27° C.

*Root description.*—Medium in thickness, fibrous; typically white in color, actual color of the roots is dependent on substrate composition, water quality, fertilizer, substrate temperature and physiological age of roots.

*Rooting habit.*—Freely branching habit; dense.

Plant description:

*Plant form and growth habit.*—Perennial shrub; uniform, upright and columnar plant habit; vigorous growth habit and rapid growth rate.

Branching habit.—Freely branching habit, dense and bushy growth habit with about six to eight primary lateral branches each with about two to six secondary lateral branches developing per plant.

*Plant height.*—About 110 cm.

*Plant diameter* (*area of spread*).—About 65 cm.

Lateral branch description:

*Length.*—About 40 cm to 90 cm.

*Diameter.*—About 4 mm to 8 mm.

*Internode length.*—About 7 cm.

*Strength.*—Strong.

*Aspect.*—Erect to about 20° from vertical.

*Texture and luster, developing.*—Pubescent; matte; becoming woody with development.

*Color, when developing.*—Close to 147A.

*Color, developed.*—Close to 200A with pubescence, close to 199A; bark, close to 199C.

Leaf description:

*Arrangement.*—Opposite, simple.

*Length.*—About 18 cm.

*Width.*—About 5 cm.

*Shape.*—Elliptic.

*Apex.*—Acuminate.

*Base.*—Cuneate.

*Margin.*—Serrate.

*Texture and luster, upper and lower surfaces.*—Smooth, glabrous; matte.

*Venation pattern.*—Pinnate.

*Color.*—Developing leaves, upper and lower surfaces: Close to N199A. Fully expanded leaves, upper surface: Close to NN137B; venation, close to 200A. Fully expanded leaves, lower surface: Close to 147B; venation, close to 146C.

*Petioles.*—Length: About 1 cm. Diameter: About 3 mm. Texture and luster, upper and lower surfaces: Smooth, glabrous; matte. Strength: Moderately strong. Color, upper surface: Close to 200A. Color, lower surface: Close to 146C.

Flower description:

*Flower appearance and arrangement.*—Rotate flowers arranged in axillary cymes; freely flowering habit with about 400 to 500 flowers developing per inflorescence and more than 10,000 flowers developing per plant during the flowering season; flower aspect, upright to outwardly.

*Fragrance.*—Slightly fragrant; sweet, floral.

*Natural flowering season.*—Plants flower from July to August in Michigan; flowers not persistent.

*Inflorescence diameter.*—About 6 cm.

*Inflorescence height.*—About 3 cm.

*Flower buds.*—Length: About 4 mm. Diameter: About 2 mm. Shape: Oblong. Texture and luster: Smooth, glabrous; matte. Color: Close to 75C to 75D.

*Flower diameter.*—About 5 mm.

*Flower depth.*—About 8 mm.

*Petals.*—Quantity and arrangement: Four petals arranged in a single whorl; not fused. Length: About 1.5 mm. Width: About 2 mm. Shape: Roughly globose. Apex: Obtuse. Base: Truncate. Margin: Entire; not undulate. Texture and luster, upper and lower surfaces: Smooth and silky, glabrous; matte. Color: When opening and fully opened, upper surface: Close to 75B; venation, close to 75B; color does not change with subsequent development. When opening and fully opened, lower surface: Close to 75B; venation, close to 75B; color does not change with subsequent development.

*Sepals*.—Quantity and arrangement: Four sepals arranged in a single whorl; sepals are minute, inconspicuous and difficult to measure due to their size; sepal length is less than 0.25 mm.

*Pedicels*.—Length: About 5 mm. Diameter: About 2 mm. Strength: Moderately strong. Aspect: About 45° from stem axis. Texture and luster: Coarse, glabrous; matte. Color: Close to 146C.

*Reproductive organs*.—Stamens: Quantity per flower: Four. Filament length: About 3 mm. Filament color: Close to N155B. Anther size: About 2 mm by 1 mm. Anther shape: Oblong. Anther color: Close to 8A. Pollen amount: Moderate. Pollen color: Close to 8A. Pistils: Quantity per flower: One. Pistil length: About 7 mm. Stigma shape: Globular. Stigma diameter: About 0.5 mm. Stigma color: Close to N155B. Style length: About 6 mm. Style color: Close to N155B. Ovary color: Close to 146C. Fruits: Quantity per flower: Potentially, one; thousands of fruits developing per plant. Length: About 5 mm. Diameter: About 5 mm. Shape: Spherical. Texture and luster: Smooth, glabrous; glossy. Color: Close to 77A. Seeds: Quantity per fruit: Four. Length: About 2 mm. Diameter: About 1.5 mm. Color: Close to 157A.

Garden performance: Plants of the new *Callicarpa* have been observed to have good garden performance and to tolerate rain, wind and to be suitable for USDA Zones 5 through 8.

Pathogen & pest resistance: To date, plants of the new *Callicarpa* have not been shown to be resistant to pathogens and pests common to *Callicarpa* plants.

It is claimed:

1. A new and distinct *Callicarpa* plant named 'SMNCJLIEP' as herein illustrated and described.

* * * * *